United States Patent [19]
Cho

[11] Patent Number: 5,738,512
[45] Date of Patent: Apr. 14, 1998

[54] TOOL FOR FASTENING RINGS TO AN ORTHODONTIC BRACKET AND METHOD THEREFOR

[76] Inventor: Kwang Hyun Cho, 3249 Hawkwood Rd., Diamond Bar, Calif. 91765

[21] Appl. No.: 374,501

[22] PCT Filed: Jul. 20, 1993

[86] PCT No.: PCT/US93/06787
§ 371 Date: Apr. 25, 1995
§ 102(e) Date: Apr. 25, 1995

[87] PCT Pub. No.: WO94/07427
PCT Pub. Date: Apr. 14, 1994

[30] Foreign Application Priority Data

Jul. 21, 1992 [KR] Rep. of Korea ............ 92-13485

[51] Int. Cl.$^6$ .................................. A61C 7/02
[52] U.S. Cl. .................................. 433/3; 433/24
[58] Field of Search .................... 433/2, 3, 4, 24; 606/140, 141

[56] References Cited

U.S. PATENT DOCUMENTS

| | | | |
|---|---|---|---|
| 3,475,818 | 11/1969 | Abrams | 433/3 |
| 3,903,601 | 9/1975 | Anderson et al. | 433/3 |
| 4,001,940 | 1/1977 | Cusato | 433/3 |
| 4,038,753 | 8/1977 | Klein | |
| 4,127,940 | 12/1978 | Shilliday | |
| 4,277,236 | 7/1981 | Kurz | 433/3 |
| 4,436,510 | 3/1984 | Klein | 433/4 |
| 4,472,137 | 9/1984 | Barone | 433/3 |
| 4,512,739 | 4/1985 | Kaniadakis | 433/3 |
| 4,921,423 | 5/1990 | Kesling | 433/3 |

Primary Examiner—Cary E. O'Connor
Attorney, Agent, or Firm—Pretty, Schroeder & Poplawski

[57] ABSTRACT

Instead of preparing the elastic rings and tool separately for the treatment, the tool of this invention can hold a number of elastic rings behind the head. When needed, an elastic ring can be pushed to the head of the tool and fixed by the indented portion of the head. Then, the elastic ring can be fastened to the bracket by the same procedure as with the traditional tools. Also, it provides a simpler way to fix the position of the elastic ring at the head of the tool. Thus, it prevents unnecessary waste of the elastic rings during the elastic ring placement at the head. The tool is designed to be disposable so that it can eliminate hygienic problem which may be caused by the repeated use of the traditional plier-type tools.

17 Claims, 3 Drawing Sheets

PRIOR ART

TOOL FOR FASTENING RINGS TO AN ORTHODONTIC BRACKET AND METHOD THEREFOR

BACKGROUND OF THE INVENTION

This design relates to a tool for fastening the elastic rings to the brackets holding an archwire in between for the orthodontic treatment. Without additional equipment or tools, the elastic ring can be fastened to the bracket easily by the tool to be described.

Prior art apparatus and methods for the orthodontic treatment can be explained by reference to FIGS. 1, 5 and 6. First, the back plate (3) of a H-shaped bracket (1) having a groove (2) is attached to the center of the tooth for the treatment. An archwire (5) is then inserted to the grooves (2) of the brackets (1) which have been attached to two teeth (4)(4'). The elastic ring is fastened to the upper and lower part (1)(1') of the H-shaped bracket (1) to fix the archwire (5). Then, the both ends of the archwire (5) are bent to achieve the desired position of the teeth (4)(4').

One of the traditional methods for fastening the elastic rings to the bracket can be explained by the FIG. 5. The elastic rings (6) are kept at the body of holder (7). Then, the elastic rings are separated one by one using a plier-type tool (not shown in the FIG. 5) and fastened to the upper and lower part (1')(1") of the bracket (1). The other method is shown in FIGS. 6(a) and (b). In this method, a number of elastic rings (6) are kept at the wire holder (8) as in FIG. 6(a). Each elastic ring is separated from the wire holder using a tool (10) having a U-shaped curvature (9). The tool is shown in FIG. 6(b). (The procedure for fastening with this tool is the same as with the tool of invention and will be described in details later).

In the method of FIG. 5, a plier-type tool is put into the ring and opened so that the expanded ring can be fastened to the upper and lower part (1')(1") of the bracket (1). Therefore, the plier-type tool needs to be positioned perpendicular to the teeth (4)(4'). Thus, in case of a molar tooth, the mouth of a patient is forced to be opened wide to the side.

Furthermore, in the method of FIG. 6(a) and (b), the procedure to separate an elastic ring (6) from the wire holder and to place at the bent portion (9) of the tool (10) is not trivial. Due to the elasticity of the ring (6), a number of elastic rings are often wasted during this procedure.

SUMMARY OF THE INVENTION

However, a tool to be described will eliminate the need of a holder because the elastic rings are kept at the rear end of the tool. When needed, an elastic ring can be pushed towards the head of the tool and placed easily at the indented portion of the head.

This tool also prevents undesired waste of the rings as in the method of FIG. 6.

BRIEF DESCRIPTION OF THE DRAWINGS

The accompanying drawings illustrate the invention. In such drawings.

DETAILED DESCRIPTION OF THE PREFERRED EMBODIMENT

Figure 2:
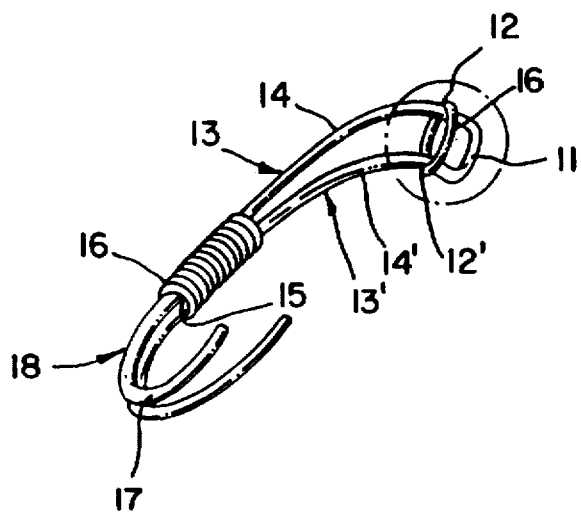
FIG. 2 shows a tool for fastening of this application.

The preferred embodiment of the tool and procedure for fastening an elastic ring to the bracket will be described in details by the FIGS. 2, 3, and 4.

The center of wire is bent to form a U-shaped head (11) of a tool. The indented portion (12)(12') of the head is also made for the placement of the elastic ring at the head. The side bars (13)(13') are made to form the elongated portion. In particular, the side bars are made to form the slanted (or convergent) portion of the tool. A number of elastic rings are held where the two wires are met together as being parallel. The end of side bars are divergent and/or bent to keep the elastic rings. Thus, a tool for fastening the elastic ring to the bracket is achieved. During the treatment, an elastic ring (16) is gradually expanded as moving towards the slanted portion (14)(14') of the head of a tool. When reached at the indented portion (12)(12') of the head (11), it is slightly shrunk and fixed at that position (12)(12').

After an elastic ring is placed at the indented portion of the head, the inner portion of the elastic ring (16) is inserted to the upper part (1') of the bracket (1) as shown in FIG. 4(a). The ring (16) is then expanded by rotating the tool (18) by 90 degrees as in FIG. 4(b). When rotated 180 degrees as in FIG. 4(c), the elastic ring (16) is separated from the tool (18) and then inserted into the lower part (1") of the bracket (1) as in FIG. 4(d). Finally, the elastic ring (16) fixes the position of the archwire (5) inserted to the grooves (2).

Figure 1:
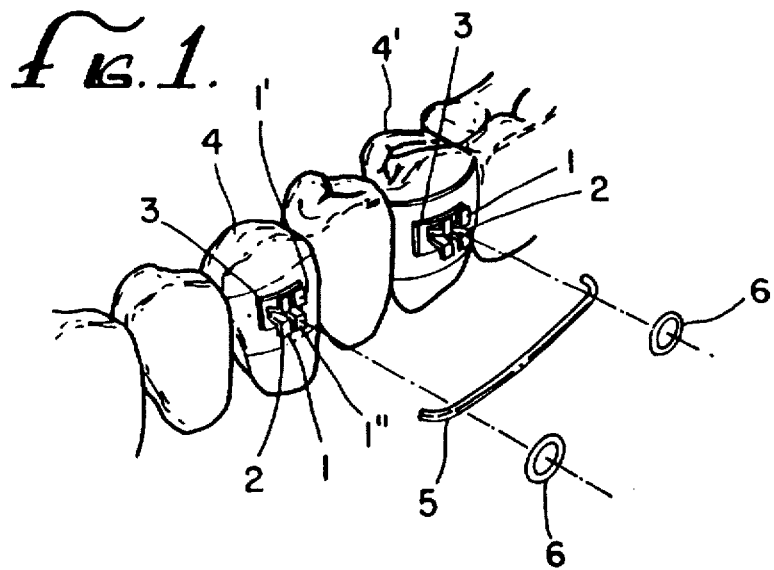
FIG. 1 shows bracket attached to teeth.
Figure 3:
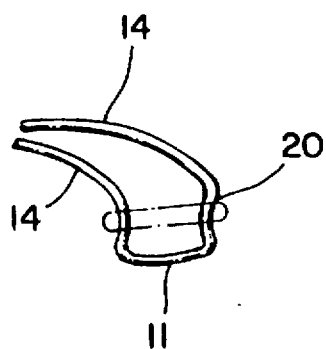
FIG. 3 shows an alternative design of a tool.
Figure 4:
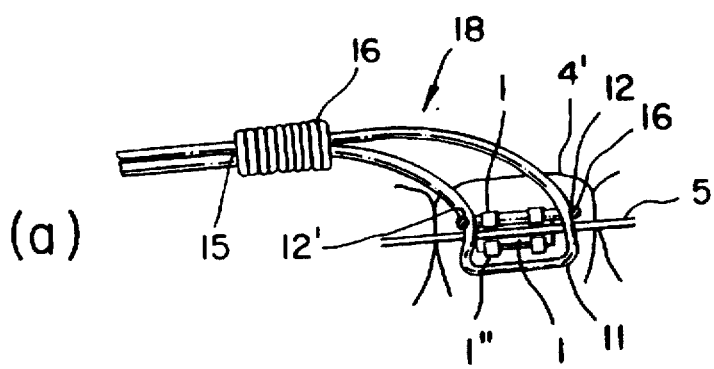
FIG. 4 shows the procedure for fastening.
Figure 4:
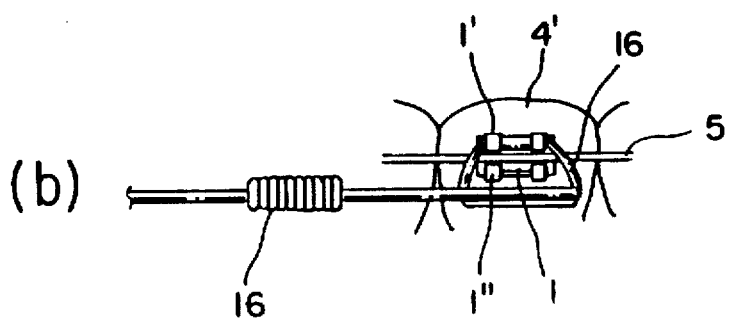
Figure 4:
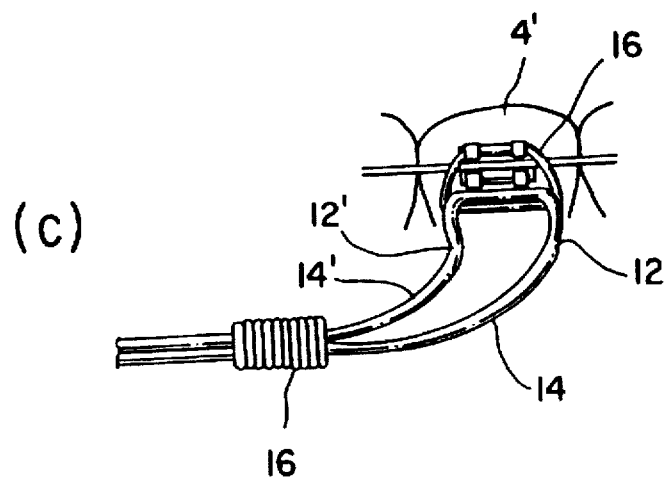
Figure 4:
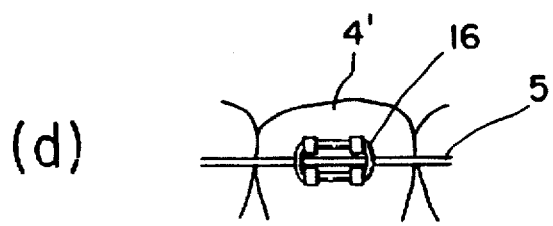
Figure 5:
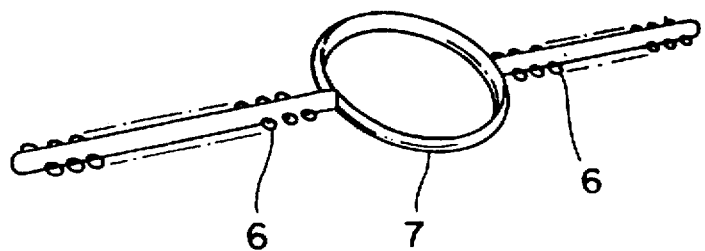
FIG. 5 shows one of the conventional holders to hold the elastic rings.
Figure 6:
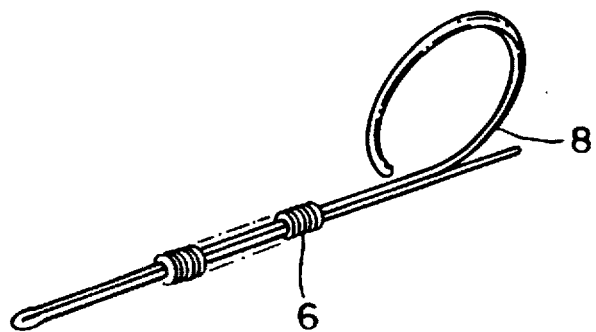
FIG. 6(a) shows another conventional holder to hold the elastic rings.
FIG. 6(b) shows a conventional tool for fastening the elastic rings for the holder in FIG. 6(a).
Figure 6:
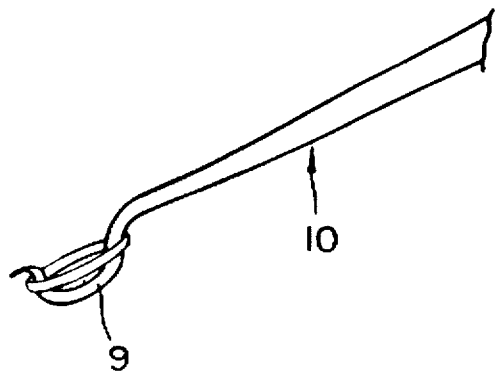

Alternative design of a tool is shown in FIG. 3. Instead of the indented portion (12) of the head, the concave portion (20) is formed at the head of the tool. With this alternative design, it is not necessary to fix the position of the elastic ring (16) at the head (11) of the tool (18).

I claim:

1. A tool for mounting an elastic ring onto a bracket for orthodontic treatment, comprising:
   a plurality of elastic rings;
   a body configured with a U-shaped head portion, and an elongated portion extending from said head portion,
   said head portion including two sides each configured with an indentation that receives said ring and stretches said ring across said sides; and
   said elongated portion being contiguous with said sides, said plurality of elastic rings stored on said elongated portion.

2. A tool in accordance with claim 1, wherein said elongated portion includes a convergent portion contiguous with said sides.

3. A tool in accordance with claim 2, wherein said convergent portion defines a degree of convergence between said head portion and said elongated portion such that said elastic rings may be readily moved between said head portion and said elongated portion.

4. A tool in accordance with claim 1, wherein said elongated portion has a predetermined curvature.

5. A tool in accordance with claim 1, wherein said sides of said head portion are separated by a distance corresponding to dimensions of the bracket.

6. A tool in accordance with claim 1, wherein said head portion is angularly offset from said elongated portion.

7. A tool in accordance with claim 1, wherein each of said plurality of elastic rings defines an opening through which said elongated portion extends.

8. A tool for mounting an elastic ring onto a bracket for orthodontic treatment, comprising:

a plurality of elastic rings;

a body configured with a U-shaped head portion, and an elongated portion, said head portion including two sides, one of said sides having a concave portion that receives said ring and stretches said ring across said sides; and said elongated portion being contiguous with said sides, said plurality of elastic rings stored on said elongated portion.

9. A tool in accordance with claim 8, wherein said elongated portion includes a convergent portion contiguous with said sides.

10. A tool in accordance with claim 9, wherein said convergent portion defines a degree of convergence between said head portion and said elongated portion such that said elastic rings may be readily moved between said head portion and said elongated portion.

11. A tool in accordance with claim 8, wherein said elongated portion has a predetermined curvature.

12. A tool in accordance with claim 8, wherein said sides of said head portion are separated by a distance corresponding to dimensions of the bracket.

13. A tool in accordance with claim 8, wherein said head portion is angularly offset from said elongated portion.

14. A tool in accordance with claim 8, wherein each of said plurality of elastic rings defines an opening through which said elongated portion extends.

15. A method for attaching a holding ring to upper and lower pairs of projections of an orthodontic bracket, said bracket having a base affixed to a labial surface of a tooth and defining a plane substantially parallel therewith, comprising the steps of:

providing a plurality of elastic rings, each defining an opening;

providing a tool configured with a U-shaped head portion, and an elongated portion extending from said head portion, said head portion including two sides and a base, said sides defining a head plane, each of said sides configured with an indentation that receives said ring and stretches said ring across said sides, said elongated portion contiguous with said sides and extending through said openings of said plurality of elastic rings;

moving one of said rings toward said head portion from said elongated portion, until said one ring is received in said indentations;

manipulating the tool to mount the ring on one of said pairs of projections of said bracket and orienting said tool such that said head plane of said head portion is substantially parallel with said labial surface;

rotating the tool using one of said sides of said head portion as a fulcrum against the labial surface of said tooth to mount the ring on said other pair of projections of said bracket.

16. A method in accordance with claim 15, wherein said bracket provides a slot between said pairs of projections that receives an archwire, and said manipulating step further comprises the step of:

manipulating the tool such that it remains substantially parallel with said archwire.

17. A method in accordance with claim 16, wherein said step of rotating includes rotating the tool substantially 180 degrees such that said head plane of said head portion after rotation is again substantially parallel with said labial surface.

* * * * *